(12) United States Patent
Silverberg

(10) Patent No.: US 12,247,014 B2
(45) Date of Patent: Mar. 11, 2025

(54) 2,3-DIARYL-1,3-THIAZEPAN-4-ONES COMPOUNDS AND METHODS FOR MAKING

(71) Applicant: The Penn State Research Foundation, University Park, PA (US)

(72) Inventor: Lee J. Silverberg, Allentown, PA (US)

(73) Assignee: The Penn State Research Foundation, University Park, PA (US)

( * ) Notice: Subject to any disclaimer, the term of this patent is extended or adjusted under 35 U.S.C. 154(b) by 702 days.

(21) Appl. No.: 17/610,022

(22) PCT Filed: May 8, 2020

(86) PCT No.: PCT/US2020/032243
§ 371 (c)(1),
(2) Date: Nov. 9, 2021

(87) PCT Pub. No.: WO2020/231870
PCT Pub. Date: Nov. 19, 2020

(65) Prior Publication Data
US 2022/0227723 A1 Jul. 21, 2022

Related U.S. Application Data

(60) Provisional application No. 62/846,218, filed on May 10, 2019.

(51) Int. Cl.
*C07D 281/02* (2006.01)
(52) U.S. Cl.
CPC .................. *C07D 281/02* (2013.01)
(58) Field of Classification Search
CPC .................................... C07D 281/02
See application file for complete search history.

(56) References Cited

U.S. PATENT DOCUMENTS 3,082,209 A 3/1963 Surrey et al.

FOREIGN PATENT DOCUMENTS

| CN | 102653526 A | 9/2012 |
| CN | 102786493 A | 11/2021 |
| WO | 2008/112674 A1 | 9/2008 |

OTHER PUBLICATIONS

Written Opinion of the International Searching Authority for PCT/US2020/032249, dated Oct. 5, 2020.
International Search Report for PCT/US2020/032249, dated Oct. 5, 2020.
Silverberg et al., Synthesis and Spectroscopic Properties of 2,3-Diphenyl-1,3-thiaza-4-one Heterocycles, International Journal of Chemistry, 2015, pp. 150-162, vol. 7, No. 2, Canada.
PubChem CID 44517771, 2009, 2, PubChem, available: https://pubchem.ncbi.nlm.nih.gov/compound/44517771.
PubChem CID 22090046, 2007, 2, PubChem, available: https://pubchem.ncbi.nlm.nih.gov/compound/22090046.
PubChem CID 139088178, 2019, PubChem, available: https://pubchem.ncbi.nlm.nih.gov/compound/139088178.
PubChem CID 10490981, 2006, 2, PubChem, available: https://pubchem.ncbi.nlm.nih.gov/compound/10490981.
PubChem CID 139086145, 2019, 2, PubChem, available: https://pubchem.ncbi.nlm.nih.gov/compound/139086145.
Lee J. Silverberg et al., Synthesis and Properties of a Series of Novel 2-Aryl-3-Phenyl-2,3-Dihydro-4H-1,3-Benzothiazin-4-Ones, Arkivoc, 2016, pp. 122-143, vol. 2016, No. 6.
Mogilaiah K. et al., Synthesis and Antimicrobial Activity of 1,8-Naphthyridinyl-4-Thiazolidinones/1,3-Thiazin-4-Ones/2-Azetidinones, Indian Journal of Chemistry, Section B, 1999, pp. 495-500, vol. 38B, No. 4.
Nagham Mahmood Aljamali, Synthesis and Characterization of New Cycles of Selenazane and Thizane, The Pharma Innovation, 2013, pp. 73-79, vol. 1, No. 11.
Hemant P. Yennawar et al., Crystal Structure of N-[(2S, 5R)-4-oxo-2,3-diphenyl-1,3-thiazinan-5-yl]acetamide 0.375-hydrate, Acta Crsytallographica Section E, 2015, pp. 62-64, vol. 71(Pt 1).

*Primary Examiner* — Paul V Ward
(74) *Attorney, Agent, or Firm* — Buchanan Ingersoll & Rooney PC

(57) ABSTRACT

A compound with the following general formula (I) and a general method for making this compound are provided, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$ are each independently selected from the group that includes H, halogen, nitro, cyano, alkyl, aryl, alkoxy, cycloalkyl, heteroalkyl, heterocyclyl, aralkyl, heteroaryl and heteroaralkyl.

7 Claims, No Drawings

2,3-DIARYL-1,3-THIAZEPAN-4-ONES COMPOUNDS AND METHODS FOR MAKING

CROSS-REFERENCE TO RELATED APPLICATIONS

This application claims the benefit of U.S. Provisional Patent Application No. 62/846,218, filed on May 10, 2019, which is incorporated by reference in its entirety.

BACKGROUND OF THE INVENTION

Field of the Invention

The present invention relates to compounds with a seven-membered 1,3-thiazepan-4-one ring system.

The seven-membered 1,3-thiazepan-4-one ring system, like the similar six-membered 1,3-thiazin-4-one and five-membered 1,3-thiazolidin-4-one systems, is biologically active and of potential medicinal use. For example, the Bristol-Myers Squibb ACE/NEP inhibitor omapatrilat advanced to Phase II clinical trials (Graul, A., Leeson, P.; Castalier, J. *Drugs Future,* 1999, 24, 269-277; Robl, J. A., et al. *J. Med. Chem.* 1997, 40, 1570-1577; Tabrizchi, R. *Curr. Opin. Investig. Drugs,* 2001, 2, 1414-1422; Cozier, G. E.; Arendse, L. B.; Schwager, S. L.; Sturrock, E. D.; Acharya, K. R. *J. Med. Chem.* 2018, 61, 10141-10154).

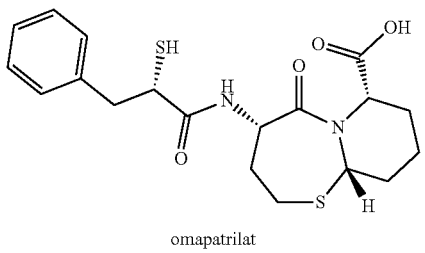 [SMILES: O=C(N[C@H]1CCS[C@H]2CCC[C@@H](C(=O)O)N2C1=O)[C@@H](S)Cc1ccccc1]

omapatrilat

In fact, nearly all of the known compounds with this ring system are related in structure to omapatrilat.

Because of their biological activity and potential medicinal use, there is a need for 2,3-diaryl-1,3-thiazepan-4-ones compounds and methods for making these compounds.

SUMMARY OF THE INVENTION

Embodiments of this invention are directed to 2,3-diaryl-1,3-thiazepan-4-one compounds.

One embodiment is directed to a compound of Formula I:

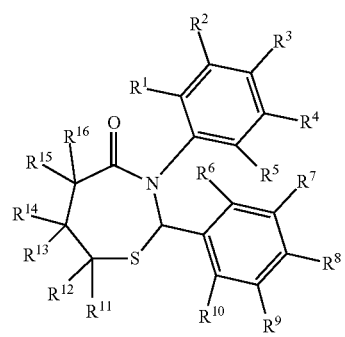

I $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$ are each independently selected from the group that includes H, halogen, nitro, cyano, alkyl, aryl, alkoxy, cycloalkyl, heteroalkyl, heterocyclyl, aralkyl, heteroaryl and heteroaralkyl. The alkyl, aryl, alkoxy, cycloalkyl, heteroalkyl, heterocyclyl, aralkyl, heteroaryl and heteroaralkyl may be optionally substituted with one or more of methyl, ethyl, halogen, nitro, methoxy, or cyano groups. If $R^1$, $R^2$, $R^3$, $R^4$, $R^5$, $R^6$, $R^7$, $R^8$, $R^9$, $R^{10}$, $R^{11}$, $R^{12}$, $R^{15}$ and $R^{16}$ are all hydrogen, $R^{13}$ and $R^{14}$ are not bonded to each other to form a cyclopropyl group.

In another embodiment, at least one of $R^1$, $R^2$, $R^3$, $R^4$, $R^5$, $R^6$, $R^7$, $R^8$, $R^9$ and $R^{10}$ is not hydrogen, and $R^{13}$ and $R^{14}$ are bonded to each other to form a cyclopropyl group.

In another embodiment, the compound is

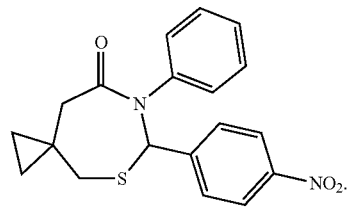 [SMILES: O=C1CC2(CC2)CSC(c2ccc([N+](=O)[O-])cc2)N1c1ccccc1]

In another embodiment, the compound is

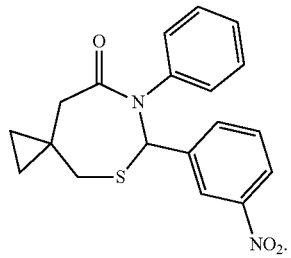 [SMILES: O=C1CC2(CC2)CSC(c2cccc([N+](=O)[O-])c2)N1c1ccccc1]

In another embodiment, the compound is

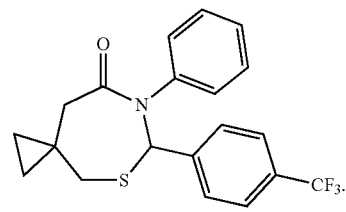 [SMILES: O=C1CC2(CC2)CSC(c2ccc(C(F)(F)F)cc2)N1c1ccccc1]

In another embodiment, the compound is

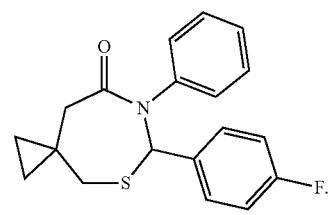 [SMILES: O=C1CC2(CC2)CSC(c2ccc(F)cc2)N1c1ccccc1]

In another embodiment, the compound is

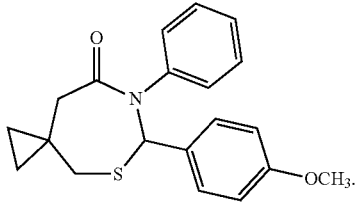 [SMILES: COc1ccc(C2SCC3(CC3)CC(=O)N2c2ccccc2)cc1]

Other aspects and advantages of the invention will be apparent from the following description and the appended claims.

DETAILED DESCRIPTION OF THE INVENTION

Definitions

While the terms used herein are believed to be well understood by one of ordinary skill in the art, definitions are set forth herein to facilitate explanation of the subject matter disclosed herein.

Unless defined otherwise, all technical and scientific terms used herein have the same meaning as commonly understood by one of ordinary skill in the art to which the subject matter disclosed herein belongs. Although any methods, devices, and materials similar or equivalent to those described herein can be used in the practice or testing of the presently disclosed subject matter, representative methods, devices, and materials are described herein.

The terms "a," "an," and "the" refer to "one or more" when used in this application, including the claims. The use of the word "a" or "an" when used in conjunction with the term "comprising" in the claims and/or the specification may mean "one," but it is also consistent with the meaning of "one or more," "at least one," and "one or more than one."

All references to singular characteristics or limitations of the present disclosure shall include the corresponding plural characteristic(s) or limitation(s) and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods and devices of the present disclosure, including components thereof, can comprise, consist of, or consist essentially of the essential elements and limitations of the embodiments described herein, as well as any additional or optional components or limitations described herein or otherwise useful.

Unless otherwise indicated, all numbers expressing physical dimensions, quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently disclosed subject matter.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The term "alkyl" includes branched, straight chain and cyclic, substituted or unsubstituted saturated aliphatic hydrocarbon groups. Alkyl groups can comprise about 1 to about 24 carbon atoms ("C1-C24"), about 7 to about 24 carbon atoms ("C7-C24"), about 8 to about 24 carbon atoms ("C8-C24"), or about 9 to about 24 carbon atoms ("C9-C24"). Alkyl groups can also comprise about 1 to about 8 carbon atoms ("C1-C8"), about 1 to about 6 carbon atoms ("C1-C6"), or about 1 to about 3 carbon atoms ("C1-C3"). Examples of C1-C6 alkyl groups include, but are not limited to, methyl, ethyl, propyl, isopropyl, butyl, sec-butyl, tert-butyl, pentyl, isopentyl, neopentyl, hexyl, isohexyl, cyclohexyl, cyclohexylinethyl, cyclopropylrnethyl and neohexyl radicals.

The term "aryl" includes a 6- to 14-membered monocyclic, bicyclic or tricyclic aromatic hydrocarbon ring system. Examples of an aryl group include phenyl and naphthyl.

The term "aralkyl" refers to an aryl-alkyl group wherein aryl and alkyl are as previously described.

The term "heteroaryl" includes an aromatic heterocycle ring of 5 to 14 members and having at least one heteroatom selected from nitrogen, oxygen and sulfur, and containing at least 1 carbon atom, including monocyclic, bicyclic, and tricyclic ring systems. Representative heteroaryls are triazolyl, tetrazolyl, oxadiazolyl, pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, pyrimidyl, oxetanyl, azepinyl, piperazinyl, morpholinyl, dioxanyl, thietanyl and oxazolyl.

As used herein, the term "halogen" means F, Cl, Br or I.

The following description is of exemplary embodiments that are presently contemplated for carrying out the present invention. This description is not to be taken in a limiting sense, but is made merely for the purpose of describing the general principles and features of the present invention. The scope of the present invention is not limited by this description.

The present invention is directed to a class of 2,3-diaryl-1,3-thiazepan-4-ones 1 and methods to make them.

A general synthetic scheme is as follows:

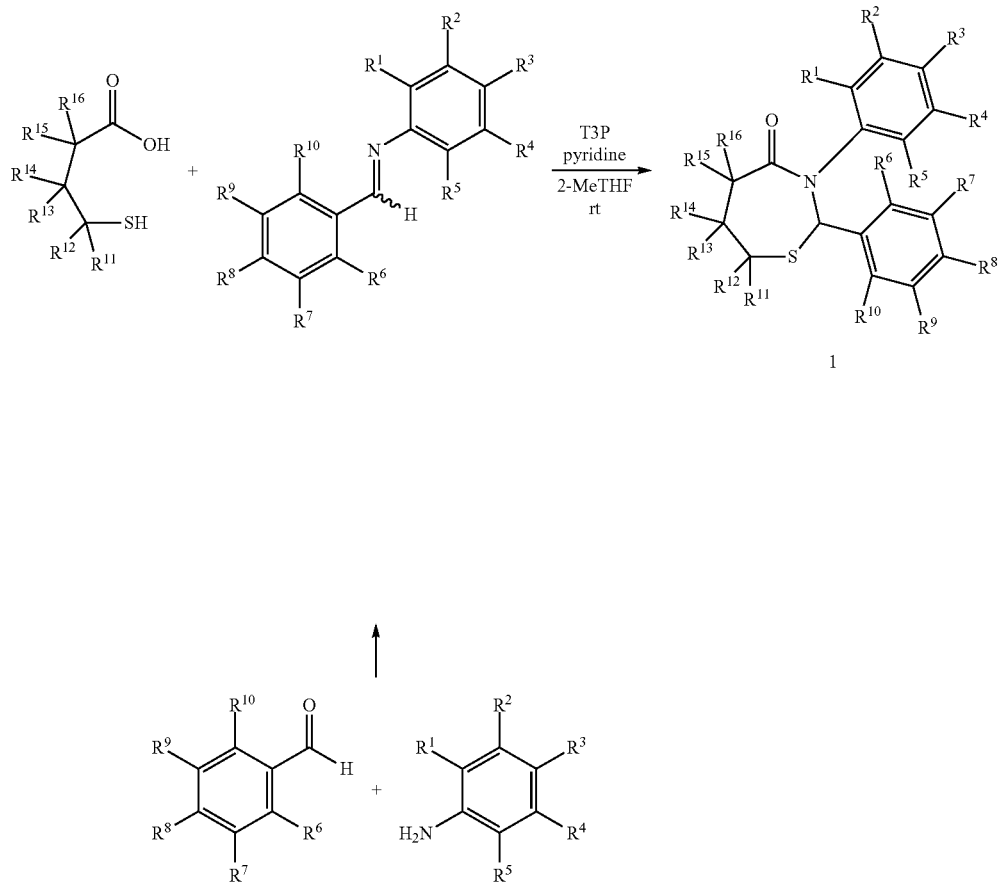

$R^1, R^2, R^3, R^4, R^5, R^6, R^7, R^8, R^9, R^{10}, R^{12}, R^{13}, R^{14}, R^{15}$ and $R^{16}$ are each independently selected from the group that includes H, halogen, nitro, cyano, alkyl, aryl, alkoxy, cycloalkyl, heteroalkyl, heterocyclyl, aralkyl, heteroaryl and heteroaralkyl.

General Synthetic Procedure: A two-necked 25-mL round bottom flask was oven-dried, cooled under $N_2$, and charged with a stir bar and an imine (6 mmol), or alternatively the precursor aldehyde and amine (6 mmol each). 2-Methyltetrahydrofuran (2.3 mL) was added and the solution was stirred. Pyridine (1.95 mL, 24 mmol) was added and then [1-(sulfanylmethyl)cyclopropyl] acetic acid (0.877 g, 6 mmol) was added. Finally, 2,4,6-tripropyl-1,3,5,2,4,6-trioxatriphosphorinane-2,4,6-trioxide (T3P) in 2-methyltetrahydrofuran (50 weight percent; 7.3 mL, 12 mmol) was added. The reaction was stirred at room temperature and followed by TLC, then poured into a separatory funnel with dichloromethane (20 mL). The mixture was washed with water (10 mL). The aqueous was then extracted twice with dichloromethane (10 mL each). The organics were combined and washed with saturated sodium bicarbonate (10 mL) and then saturated sodium chloride (10 mL). The organic was dried over sodium sulfate and concentrated under vacuum to give a crude mixture. Further purification was carried out as indicated below for each compound.

EXAMPLE 1

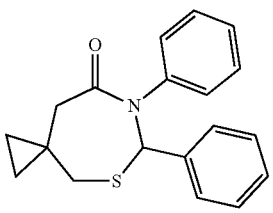

1a 6,7-diphenyl-5-thia-7-azaspiro[2.6]nonan-8-one 1a: After workup to give a crude yellow liquid, crystals slowly grew. The crystals were collected by vacuum filtration and washed repeatedly with cold 2-propanol, leaving white crystals (0.424 g, 24%). m.p.: 144-145° C. $^1$H NMR (CDCl$_3$): δ(ppm): 7.56 (d, 2H, J=6.1 Hz), 7.40-7.25 (m, 8H), 6.17 (s, 1H), 3.12 (d, 1H, J=12.2 Hz), 2.72 (d, 1H, J=13.4 Hz), 2.54 (br. s, 2H), 0.9 (m, 1H), 0.77-0.68 (m, 2H), 0.65-0.62 (m, 1H).

EXAMPLE 2

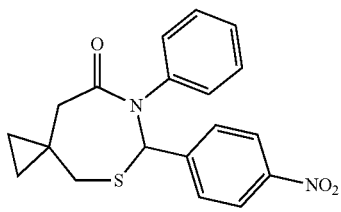

6-(4-nitrophenyl)-7-phenyl-5-thia-7-azaspiro[2.6]nonan-8-one 1b: Chromatography on 30 g flash silica gel with mixtures of ethyl acetate and hexanes gave a solid. Recrystallization from ethyl acetate gave white crystals (0.1804 g, 9%). m.p.: 207-209° C. (decomposition). $^1$H NMR (CDCl$_3$): δ(ppm): 8.22 (d, 2H, J=8.4 Hz), 7.70 (d, 2H, J=6.6 Hz), 7.35 (m, 2H), 7.27 (m, 3H), 6.26 (s, 1H), 2.97 (br. s, 1H), 2.73 (br. s, 2H), 2.59 (d, 1H, J=14.3 Hz), 0.91 (m, 1H), 0.81 (m, 1H), 0.74 (m, 1H), 0.68 (m, 1H).

EXAMPLE 3

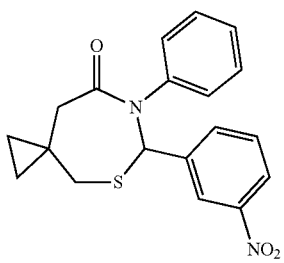

6-(3-nitrophenyl)-7-phenyl-5-thia-7-azaspiro[2.6]nonan-8-one 1c: Chromatography on 30 g flash silica gel with mixtures of ethyl acetate and hexanes gave a solid (0.6728 g). Recrystallization from 2-propanol gave crystals (0.5192 g, 26%). m.p.: 184-185° C. $^1$H NMR (CDCl$_3$): δ(ppm): 8.28 (bs, 1H), 8.07 (d, 1H, J=8.1 Hz), 7.68 (br. s, 1H), 7.44 (t, 1H, J=8.1 Hz), 7.25 (m, 2H), 7.17 (m, 3H), 6.20 (s, 1H), 2.85 (br. s, 1H), 2.72 (br. s, 2H), 2.46 (d, 1H, J=14.7), 0.81 (m, 1H), 0.74 (dt, 1H, J=9.0, 4.7 Hz), 0.66 (dt, 1H, J=9.9, 5.0 Hz), 0.59 (m, 1H).

EXAMPLE 4

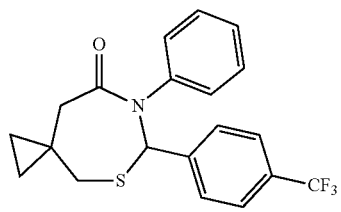

6-(4-(trifluoromethyl)phenyl)-7-phenyl-5-thia-7-azaspiro[2.6]nonan-8-one 1d: Chromatography on 30 g flash silica gel with mixtures of ethyl acetate and hexanes gave a white solid. Recrystallization from 2-propanol gave white crystals (0.8998 g, 40%). m.p.: 158-160° C. $^1$H NMR (CDCl$_3$): δ(ppm): 7.66 (m, 4H), 7.33, (m, 5H), 6.18 (s, 1H), 3.09 (d, 1H, J=14.8 Hz), 3.06 (dd, 1H, J=30.8, 17.9 Hz), 2.7-2.5 (m, 3H). 0.91 (m, 1H), 0.79-0.62 (m, 3H).

EXAMPLE 5

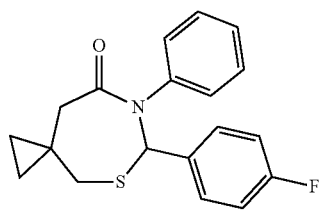

6-(4-fluorophenyl)-7-phenyl-5-thia-7-azaspiro[2.6]nonan-8-one 1e: Chromatography on 30 g flash silica gel with mixtures of ethyl acetate and hexanes gave a solid (0.6728 g). Recrystallization from ethyl acetate/hexanes gave white crystals (0.5296 g, 27%). m.p.: 113-117° C. $^1$H NMR (CDCl$_3$): δ(ppm): 7.44 (br. s, 2H), 7.34 (t, 2H, J=7.6 Hz), 7.26 (m, 3H), 7.03 (t, 2H, J=8.5 Hz), 6.19 (s, 1H), 2.97 (m, 1H), 2.80-2.60 (m, 3H), 0.91 (m, 1H), 0.82-0.63 (m, 3H).

EXAMPLE 6

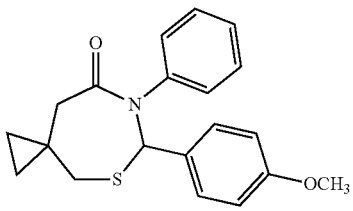

6-(4-methoxy)-7-phenyl-5-thia-7-azaspiro[2.6]nonan-8-one 1f: Chromatography on 30 g flash silica gel with mixtures of ethyl acetate and hexanes gave an oil (0.3139 g). Recrystallization from 2-propanol gave (0.1673 g, 8%). m.p.: 145-149° C.

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

REFERENCES

All references cited herein including those below are hereby incorporated by reference in their entirety.

H. P. Yennawar and L. J. Silverberg, "6,7-Diphenyl-5-thia-7-azaspiro[2.6]nonan-8-one," *Acta Cryst., Sect. E: Struct. Rep. Online* 2013, E69, o1659.

L. J. Silverberg, C. N. Pacheco, A. Lagalante, K. C. Cannon, J. T. Bachert, Y. Xie, L. Baker, and J. A. Bayliff, "Synthesis and Spectroscopic Properties of 2,3-Diphenyl-1,3-thiaza-4-one Heterocycles," *Int. J. Chem.* (Toronto, ON, Can.) 2015, 7 (2), 150-162.

I claim:

1. A compound of Formula 1:

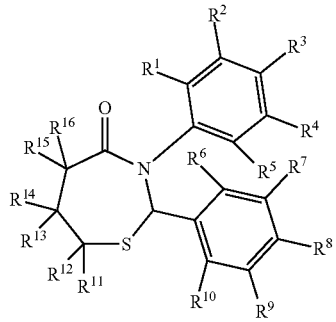

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$ are each independently selected from the group consisting of H, halogen, nitro, cyano, alkyl, aryl, alkoxy, cycloalkyl, heteroalkyl, heterocyclyl, aralkyl, heteroaryl and heteroaralkyl, wherein the alkyl, aryl, alkoxy, cycloalkyl, heteroalkyl, heterocyclyl, aralkyl, heteroaryl and heteroaralkyl may be optionally substituted with one or more of methyl, ethyl, halogen, nitro, methoxy, or cyano groups, and wherein if $R^1$, $R^2$, $R^3$, $R^4$, $R^5$, $R^6$, $R^7$, $R^8$, $R^9$, $R^{10}$, $R^{11}$, $R^{12}$, $R^{15}$ and $R^{16}$ are all hydrogen, $R^{13}$ and $R^{14}$ are not bonded to each other to form a cyclopropyl group.

2. The compound of claim 1, wherein at least one of $R^1$, $R^2$, $R^3$, $R^4$, $R^5$, $R^6$, $R^7$, $R^8$, $R^9$ and $R^{10}$ is not hydrogen, and wherein $R^{13}$ and $R^{14}$ are bonded to each other to form a cyclopropyl group.

3. The compound of claim 2, wherein the compound is

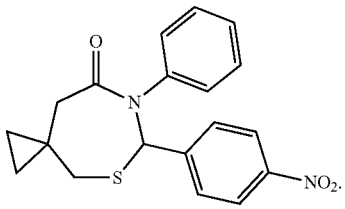 [SMILES: O=C1CC2(CC2)CSC(c2ccc([N+](=O)[O-])cc2)N1c1ccccc1]

4. The compound of claim 2, wherein the compound is

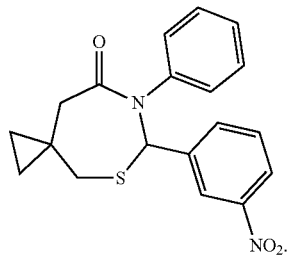 [SMILES: O=C1CC2(CC2)CSC(c2cccc([N+](=O)[O-])c2)N1c1ccccc1]

5. The compound of claim 2, wherein the compound is

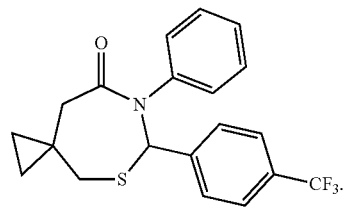 [SMILES: O=C1CC2(CC2)CSC(c2ccc(C(F)(F)F)cc2)N1c1ccccc1]

6. The compound of claim 2, wherein the compound is

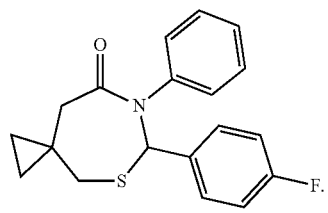 [SMILES: O=C1CC2(CC2)CSC(c2ccc(F)cc2)N1c1ccccc1]

7. The compound of claim 2, wherein the compound is

* * * * *